US010340037B2

(12) United States Patent
Douglass et al.

(10) Patent No.: US 10,340,037 B2
(45) Date of Patent: Jul. 2, 2019

(54) AGGREGATING A PATIENT'S DISPARATE MEDICAL DATA FROM MULTIPLE SOURCES

(71) Applicant: Allscripts Software, LLC, Raleigh, NC (US)

(72) Inventors: Matthew C. Douglass, San Francisco, CA (US); Jonathan M. Malek, Sacramento, CA (US)

(73) Assignee: Allscripts Software, LLC, Raleigh, NC (US)

( * ) Notice: Subject to any disclaimer, the term of this patent is extended or adjusted under 35 U.S.C. 154(b) by 577 days.

(21) Appl. No.: 14/493,887

(22) Filed: Sep. 23, 2014

(65) Prior Publication Data

US 2016/0085914 A1   Mar. 24, 2016

(51) Int. Cl.
*G16H 10/60* (2018.01)
*G06F 19/00* (2018.01)

(52) U.S. Cl.
CPC .............. *G16H 10/60* (2018.01); *G06F 19/00* (2013.01)

(58) Field of Classification Search
CPC .... G06F 19/322–327; G06Q 50/22–24; G16H 10/60
See application file for complete search history.

(56) References Cited

U.S. PATENT DOCUMENTS

| 8,856,188 | B2* | 10/2014 | Reiner | G06F 17/30595 |
| | | | | 707/705 |
| 2002/0120472 | A1* | 8/2002 | Dvorak | G06F 19/322 |
| | | | | 705/3 |
| 2006/0080312 | A1* | 4/2006 | Friedlander | G06F 19/322 |
| 2009/0083664 | A1 | 3/2009 | Bay et al. | |
| 2013/0024206 | A1* | 1/2013 | Hughes | G06Q 10/10 |
| | | | | 705/3 |
| 2014/0006047 | A1 | 1/2014 | Amathnadu et al. | |

OTHER PUBLICATIONS

Non-Final Rejection dated Jul. 15, 2014 for U.S. Appl. No. 14/268,759, filed May 2, 2014; 14 pages.

* cited by examiner

*Primary Examiner* — Sheetal R Paulson
(74) *Attorney, Agent, or Firm* — Medley, Behrens & Lewis, LLC (57) ABSTRACT

In an embodiment, a computer-implemented method aggregates medical data from a plurality of source providers. In the method, medical data is received from a source provider. This medical data may be associated with patient-identification information. In order to aggregate this data with other data about the same patient, this data is then reconciled with existing patient medical data records in a medical records database to identify a master patient to whom the received medical data relates. The medical records database includes a plurality of different types of patient medical data records, and each data record is associated with a corresponding time and a corresponding source. Verification is performed to confirm that the source provider associated with the received medical data is authorized to add medical data related to the identified master patient, and finally a new medical data record containing the received medical data is written to the database.

19 Claims, 7 Drawing Sheets

| | TYPE/SOURCE | DETAILS | STATUS | |
|---|---|---|---|---|
| 220 | Office encounter<br>Dr. Epstein | Dx: Bronchitis, not specified as acute or chronic; Esophageal reflux; Benign essential...<br>Orders: | Draft<br>10/14/2013 | ☐ |
| 222 | Refill request<br>Patient | 3 days overdue<br>Guidance Ctr Westside has sent you a refill request for Sarah... | Requested<br>09/22/2013 | ☐ |
| 224 | Home encounter<br>Dr. Murphy | Dx: Benign essential hypertension<br>Orders: Lisinopril oral tablet 30mg; CBC w/differential | Signed 🔒<br>05/17/2013 | ☐ |
| 226 | CBC<br>Dr. Epstein | WBC, Hct, Hbg, MCV, MCH, MCHC, RDW<br>Quest 108234087134 | Signed 🔒<br>02/12/2013 | ☐ |
| 228 | Chest x-ray, frontal<br>Dr. Epstein | A single, 3cm relatively thin-walled cavity is noted in the left midlung. This finding is...<br>MediScan 20873432-8 | Signed 🔒<br>02/11/2013 | ☐ |
| 230 | Appt. request<br>Patient | My rash isn't getting any better, can I come later this week for a followup appoin... more | Replied<br>02/08/2013 | ☐ |

Sarah Williams  29 Female  02/05/1984  Blueshield

All event types ∨ [Actions ∨]

AGGREGATING A PATIENT'S DISPARATE MEDICAL DATA FROM MULTIPLE SOURCES

BACKGROUND

Field

This field is generally related to aggregating and storing electronic health records from a plurality of sources and presenting electronic health records on a display.

Background

Electronic Health Records

Medical records related to a patient's health information are essential to the practice of medical care. Traditionally, medical records were paper-based documents. The emergence of electronic medical records (EMRs), which are digital version of the paper chart that contains all of a patient's medical history from one medical practice, offers medical professionals and patients with new functionalities and efficiencies that paper-based medical records cannot provide. An electronic health record (EHR) is a collection of electronically stored information about an individual patient's medical history. EHRs may contain a broad range of data, including demographics, medical history, medication history, allergies, immunization records, laboratory test results, radiology images, vital signs, personal statistics like age and weight, and billing information. Many commercial EHR systems combine data from a number of healthcare services and providers, such as clinical care facilities, laboratories, radiology centers, and pharmacies.

EHRs are a drastic improvement over paper-based medical records. Paper-based medical records require a large amount of physical storage space. Paper records are often stored in different locations, and different medical professionals may each have different and incomplete records about the same patient. Obtaining paper records from multiple locations for review by a healthcare provider can be time consuming, complicated, and sometimes impossible. In contrast, EHR data is stored in digital format, and thus are more secure and can be accessed from anywhere. EHR systems significantly simplify the reviewing process for healthcare providers. Because records in EHRs can be linked together, EHRs vastly improve the accessibility of health records and the coordination of medical care.

EHRs also decrease the risk of misreading errors by healthcare professionals. Poor legibility is often associated with handwritten, paper medical records, which can lead to medical errors. EHRs, on the other hand, are inherently legible given that they are typically stored in typeface. In addition, EHRs enhance the standardization of forms, terminology and abbreviations, and data input, which help ensure reliability of medical records, and standardization of codesets and storage of EHR data means that data from different technical information systems can be displayed in a single, unified record. Further, EHRs can be transferred electronically, thus reducing delays and errors in recording prescriptions or communicating laboratory test results.

The benefits of digitizing health records are substantial. Healthcare providers with EHR systems have reported better outcomes, fewer complications, lower costs, and fewer malpractice claim payments. But despite EHRs' potential in drastically improving the quality of medical care, only a low percentage of healthcare providers use EHR systems. While the advantages of EHRs are significant, they also carry concerns, including high costs, lost productivity during EHR implementation or computer downtime, and lack of EHR usability.

The Health Insurance Portability and Accountability Act (HIPAA), enacted in the U.S. in 1996, and as amended, established rules for use and access of protected health information (PHI). HIPAA provides restrictions on disclosure of and access to protected health information to and by third parties. HIPAA applies to information in electronic medical records, such as health information doctors and nurses input, documented conversations between a doctor and a patient, and information use to process or facilitate medical billing claims and documents. The HIPAA Security Rule, effective on Apr. 20, 2005 for most covered entities, adds additional constraints to electronic data security and the storage and transmission of PHI.

The high cost of EHR systems also significantly hinders EHR adoption. A large number of physicians without EHR systems have referred to initial capital costs as a barrier to adopting EHR systems. Cost concerns are even more severe in smaller healthcare settings, because current EHR systems are more likely to provide cost savings for large integrated institutions than for small physician offices. During the EHR system technology's setup and implementation process, productivity loss can further offset efficiency gains. The need to increase the size of information technology staff to maintain the system adds even more costs to EHR system usages.

Usability is another major factor that holds back adoption of EHRs. It is particularly challenging to develop user-friendly EHR systems. There is a wide range of data that needs to be integrated and connected. Complex information and analysis needs vary from setting to setting, among healthcare provider groups, and from function to function within a healthcare provider group. To some providers, using electronic medical records can be tedious and time consuming, and the complexity of some EHR systems renders the ERR usage less helpful. Some doctors and nurses also complain about the difficulty and the length of time to enter patients' health information into the system.

Under-utilization of EHR systems, despite incentives and mandates from the government and the tremendous potential of EHR systems in revolutionizing the healthcare system, calls for better ERR systems that are secure, cost-effective, efficient, and user-friendly.

Comprehensive EHR systems can provide capabilities far beyond simply storing patients' medical records. Because EHR systems offer healthcare providers and their workforce members the ability to securely store and utilize structured health information, EHR systems can have a profound impact on the quality of the healthcare system. In Framework for Strategic Action on Health Information Technology, published on Jul. 21, 2004, the Department of Health & Human Services (HHS) outlined many purposes for EHR services. The outlined purposes include, among other things, improving healthcare outcomes and reducing costs, reducing recordkeeping and duplication burdens, improving resource utilization, care coordination, active quality and health status monitoring, reducing treatment variability, and promoting patients' engagement in and ownership over their own healthcare.

Recent legislation has set goals and committed significant resources for health information technology (IT). One of the many initiatives of the American Recovery and Reinvestment Act of 2009 (ARRA) was "to increase economic efficiency by spurring technological advances in science and health." The Health Information Technology for Economic and Clinical Health (HITECH) Act, passed as a part of ARRA, allocated billions of dollars for healthcare providers to adopt and meaningfully use EHR systems in their practices. HITECH also mandates the Office of the National Coordinator for Health Information Technology (ONC) to define certification criteria for "Certified EHR Technology."

EHR systems satisfying "Certified EHR Technology" criteria are capable of performing a wide range of functions, including: entry and storage, transmission and receipt of care summaries, clinical decision support, patient lists and education resources, generation of public health submission data, and patient engagement tools. Entry and storage is related to the ability to enter, access and modify patient demographic information, vital signs, smoking status, medications, clinical and radiology laboratory orders and results. Transmission and receipt of care summaries involve the ability to receive, incorporate, display and transmit transition of care/referral summaries. Clinical decision support features configurable clinical decision support tools, including evidence-based support interventions, linked referential clinical decision support, and drug-drug and drug-allergy interaction checks. Patient lists and education resources include the ability to create patient lists based on problems, medications, medication allergies, demographics and laboratory test result values, and the ability to identify patient-specific education resources based on such data elements. Generating public health submission data allows users to create electronic immunization and syndromic surveillance data files that can be submitted to public health agencies. Patient engagement tools allow medical professionals to grant patients with an online means to view, download and transmit their health information to a third party, provide patients with clinical summaries after office visits, and facilitate secure-doctor patient messaging.

File Organization

Maintaining complete records of a patient's medical history is essential to quality healthcare. A single patient may have multiple healthcare providers, each of which has their own patient record and record-keeping system. Even if the patient's healthcare providers all use some form of an EHR system, the systems may store data differently and under different identifying information. As such, it is difficult for healthcare providers to share their patient records with other authorized healthcare providers.

BRIEF SUMMARY

In an embodiment, a computer-implemented method aggregates medical data from a plurality of source providers. In the method, medical data is received from a source provider. This medical data may be associated with patient-identification information. In order to aggregate this data with other data about the same patient, this data is then reconciled with existing patient medical data records in a medical records database to identify a master patient to whom the received medical data relates. The medical records database includes a plurality of different types of patient medical data records, and each patient medical data record is associated with a corresponding time and a corresponding source. Verification is performed to confirm that the source provider associated with the received medical data is authorized to add medical data related to the identified master patient, and finally a new patient medical data record containing the received medical data is written to the database.

Method and computer program product embodiments are also disclosed.

Further embodiments, features, and advantages of the invention, as well as the structure and operation of the various embodiments, are described in detail below with reference to accompanying drawings.

BRIEF DESCRIPTION OF THE DRAWINGS

The accompanying drawings, which are incorporated herein and form part of the specification, illustrate the present disclosure and, together with the description, further serve to explain the principles of the disclosure and to enable a person skilled in the relevant art to make and use the disclosure.

The drawing in which an element first appears is typically indicated by the leftmost digit or digits in the corresponding reference number. In the drawings, like reference numbers may indicate identical or functionally similar elements.

DETAILED DESCRIPTION

Overview

Physicians have traditionally kept patient records in paper files, making them only accessible to the physicians and staff within a particular practice or office. If a patient wanted to keep track of his or her medical history, it was the patient's responsibility to keep track of all events and results. With more modern EMR systems, patients are now able to access their medical history through certain healthcare providers, but this history may be spread across several different providers and institutions. Moreover, this data is not standardized across every institution, and merging the data into a single location for unified access poses a significant problem. For example, each healthcare provider or institution may identify the patient using different patient identifiers, referred to herein as a provider-specific identifier. It is not a trivial task to determine whether patient medical data from two separate institutions relate to the same individual, and some form of reconciliation must be put into place in order to make these determinations and merge or link the information under a single master patient record.

Additionally, since there is no centralized link between healthcare records of separate healthcare practices and institutions, communication and collaboration between these organizations must be accomplished manually. For example, when a primary care physician refers a patient to a specialist, the medical history from the primary care physician is typically sent to the specialist by facsimile, and any further communication must be accomplished by similar manual means. This process can be time consuming and still requires both practices to maintain a record of the communication and medical history of the patient separately.

Embodiments of the present invention address these issues by aggregating different data about a patient across multiple healthcare institutions and sources. A source, or source provider, is simply an entity that provides healthcare data about a patient. Examples may include, but are not limited to, a physician, a medical practice, a medical laboratory, and a personal healthcare device. The aggregated data can be used to provide a single point of access to a patient's medical history for healthcare professionals and patients.

In the detailed description that follows, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Data Aggregation

Figure 1:
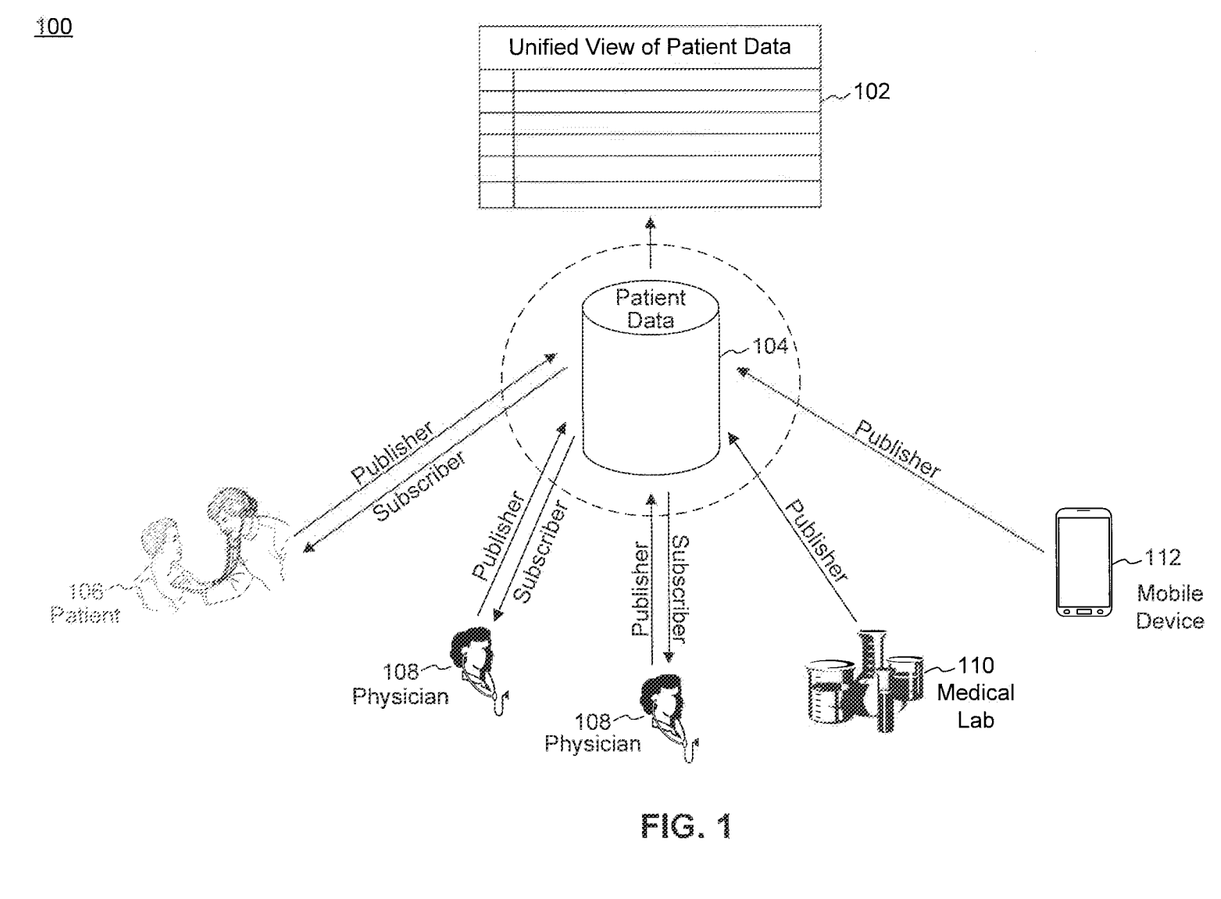
FIG. 1 is a diagram illustrating the aggregation of medical data from a plurality of source providers and the presentation of the medical data in a single, unified view, according to an embodiment.

FIG. 1 illustrates the aggregation of medical data from a plurality of source providers and the presentation of the medical data in a single, unified view, according to an embodiment.

Data related to a patient is stored in a centralized location 104, and the system leverages the familiar publish-subscribe software pattern, where publishers are able to add, or write, data about a patient to the centralized location, and subscribers are able to read the previously-written data from the centralized location. In the embodiment of FIG. 1, several sources are shown that contribute information about a single patient. In this example, the patient 106, doctors 108, a medical lab 110, and a mobile device 112 all write data about the patient to the centralized location 104. The system at the centralized location includes a medical records database, and all of the patient medical data submitted by the source providers are stored in the database. Any event or observation regarding a patient may be represented by a patient medical data record that can be stored in the medical records database. For example, information about a patient visit to a physician, test results from a medical lab, and monitoring data from a wearable medical device are all events or observations related to a patient that may be written to the medical records database. A patient medical data record may reside in a single database table or be distributed among a plurality of tables and/or database instances.

The patient medical data records in the medical records database, which together make up a patient's medical history, can be presented in a single, unified view 102. Subscribers to patient data are able to view published data about the patient in this unified view, allowing an entity to view the complete medical history of a patient in one place. An embodiment of this unified view can be seen in FIG. 2, which is described in more detail below. The embodiment presents the patient medical data records related to a specific patient in a temporally ordered timeline. The temporally ordered timeline may be created in accordance with the invention described in U.S. patent application Ser. No. 14/268,759, filed May 2, 2014, which is incorporated herein by reference in its entirety.

All entities must be authorized to publish (e.g., add) or subscribe to (e.g., view) data about a patient. This authorization may be automatic, or it may require permission from the patient or other authorizing entity. For example, a visit to a doctor may automatically authorize the doctor to publish information about the patient. In contrast, explicit patient authorization may be required before a wearable fitness device can publish data about that patient. Similarly, a referred specialist may be automatically authorized to view data about a patient. Alternatively, the specialist may require explicit permission from the patient before the specialist can view the patient data. As will be described below, embodiments of the present invention provide means for authorizing an entity to view and add medical data related to a patient.

An entity may also be authorized to view only a portion of the medical data related to a patient. In some cases, a patient may not wish to disclose his or her complete medical history to a particular entity, or certain data may not be useful to an entity. Embodiments of the present invention allow for the selective authorization of any combination of patient medical data records related to a specific patient. Example combinations may include, for example and without limitation, all data published by a particular source, all data of a particular type, all data related to a particular topic, or specifically chosen data records. For example, an embodiment allows all patient medical data records related to the sexual history or the psychiatric history of a patient to be made private from one or more entities by not authorizing the entity or entities to view these data records.

Presentation Interface

Figure 2:
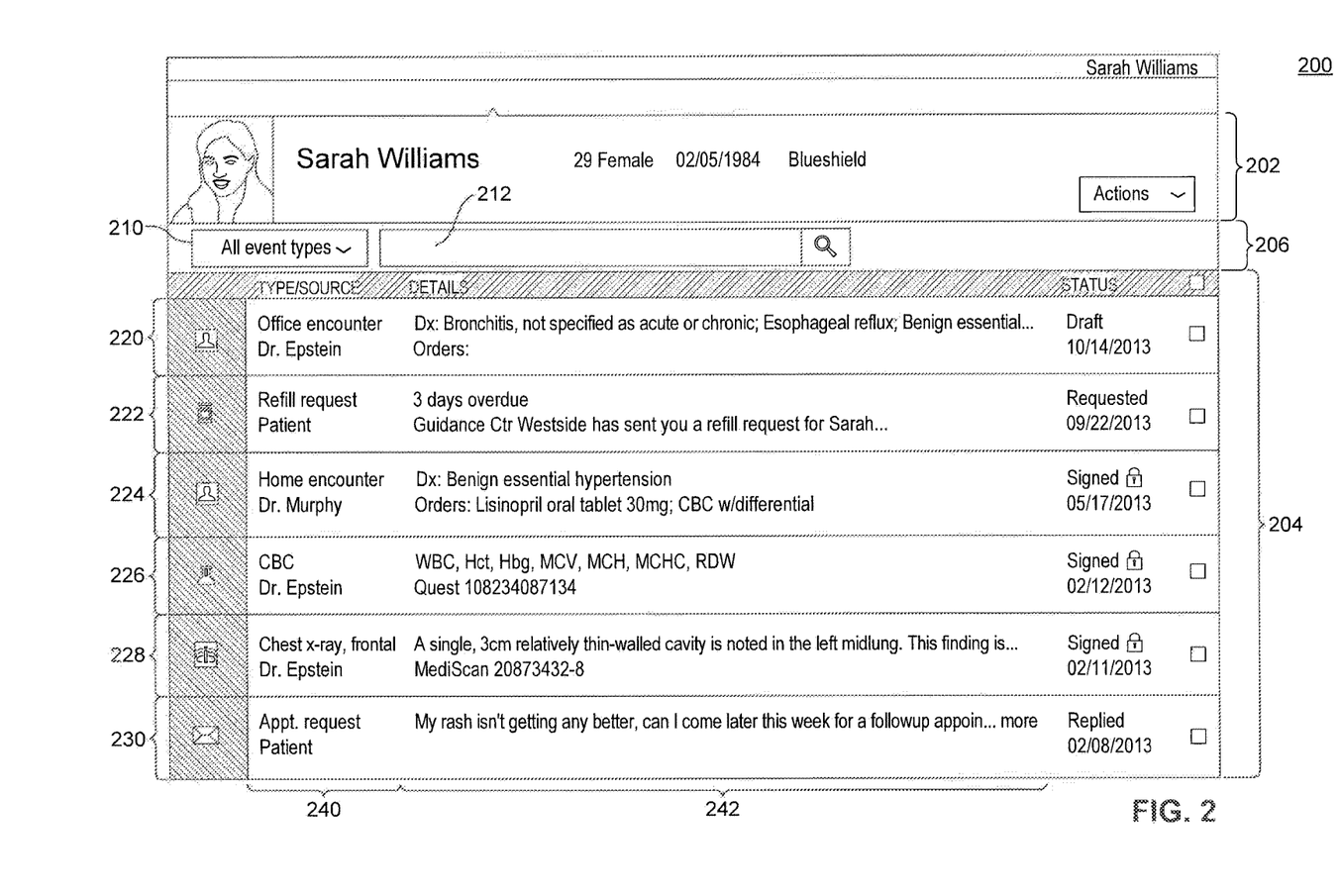
FIG. 2 is an interface that presents medical data records related to a patient from a plurality of sources in a single, unified view, according to an embodiment.

FIG. 2 shows a screen layout 200 illustrating an interface that presents a patient's disparate medical data on a unified timeline, according to an embodiment. The interface may be used, for example, by a patient viewing their complete history of care. In the embodiment shown in FIG. 2, the interface is divided into three frames: frame 202, 204, and 206. Each is discussed in turn.

Frame 202 displays demographic information about the patient. The demographic information may include, for example and without limitation, the patient's name, age, gender, date of birth, insurance provider, and likeness (such as a photograph).

Frame 204 displays a timeline with the patient's medical data. Frame 204 displays the timeline in a table with rows and columns. In particular, each patient medical data record is displayed as separately, and frame 204 includes six rows: row 220, 222, 224, 226, 228, and 230. The timeline rows represent different types of patient medical data. In the example of layout 200, rows 220 and 224 represent patient encounters, which are instances where a physician met with the patient. Rows 226 and 228 represent lab results. Row 222 represents a prescription, such as an e-prescription. Row 230 represents a message from the patient.

In the embodiment of FIG. 1, each row includes at least two columns: columns 240 and 242. Column 240 indicates the type of patient data (e.g., encounter, prescription, lab result, or message). In addition, column 240 can list the source provider (e.g., the patient, the name of the physician, lab or device that provided data). Column 242 provides a summary of the medical information represented in each row. The summary may include different types of information and may be presented differently depending on the type of patient data and the availability of associated data. But, despite these differences, the summary may be generated such that it can be presented in a regular, uniform manner as illustrated in column 242.

In frame 204, the rows of patient medical data are ordered based on time. Each data row has an associated timestamp. For example, for encounters, the timestamp may indicate when the encounter occurred; for prescriptions, the timestamp may indicate when the prescription was authorized or requested; for lab results, the timestamp may indicate when the test was conducted or when the results were reported; for device data, the timestamp may indicate when the data was collected by the device; and, for messages, the timestamp may indicate when the message was received by the system. In an embodiment, frame 204 orders the data rows in reverse chronological order, with the data rows listed from newest to oldest. In this way, an entity can scan through the data rows to quickly understand the patient's complete history of care, without a full analysis of the patient's entire electronic health record.

While providing the complete medical history may be useful, there may be instances where a patient or other entity would want to filter the data being presented. To reduce the amount of data presented, the interface provides additional user interface (UI) controls in frame 206. Other features and information describing the creation of such a temporally ordered medical record timeline may be found in U.S. patent application Ser. No. 14/268,759, filed May 2, 2014, which is incorporated herein by reference in its entirety.

Method

Figure 3:
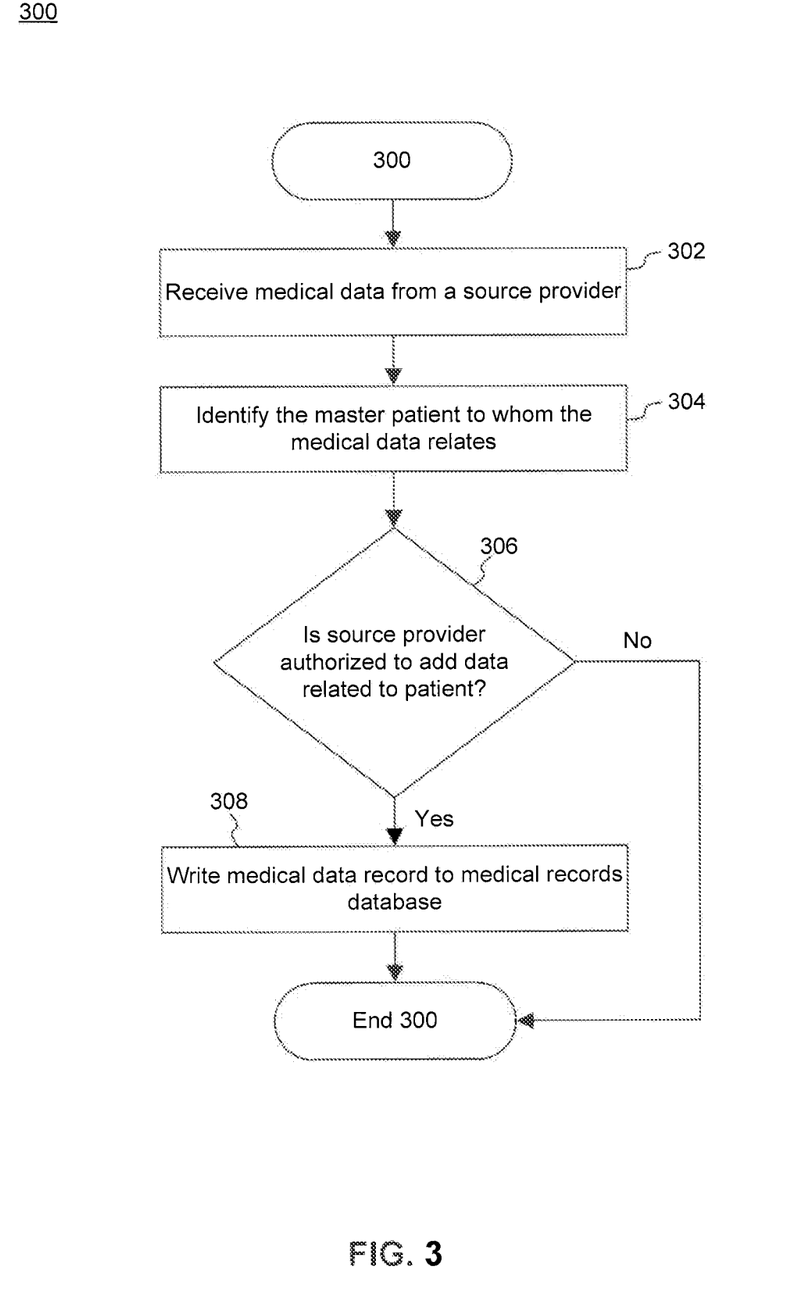
FIG. 3 is a flowchart illustrating an example method for receiving and aggregating medical data from a source provider.

FIG. 3 is a flowchart illustrating an example method for receiving and aggregating medical data at a central EHR system from a source provider.

Method 300 begins at step 302 by receiving medical data at a central EHR system from a source provider. The central EHR system may be, for example, a cloud-based EHR system such as that described in further detail with respect to FIG. 6 below. As shown in FIG. 1, examples of source providers may include, but are not limited to, a patient, a doctor or medical practice, a medical lab, and a wearable medical device. The original medical data may be transmitted from the source provider via a network, such as the Internet. In one example, the medical data is transmitted as a parameter or parameters of a hypertext transfer protocol (HTTP) request. While the medical data may include a patient identifier, such an identifier may be a provider-specific identifier, and may not match a master patient identifier by which information about the specific patient is stored within the central EHR system.

For ease of reference, the patient identifier received from the source provider will be referred to herein as the provider-specific patient identifier. Such an identifier may include, for example and without limitation, a Social Security number, a surname, a first name, a date of birth, a gender, Medical Record Number, a randomly-assigned number, and the like, or any combination thereof. While the source provider's identifier will be referred to as a provider-specific patient identifier, one of skill in the art will recognize that multiple source providers may use the same provider-specific identifier, such as the patient's Social Security number or Medical Record Number. The central EHR system may identify an individual patient under a same or different identifier. The patient identifier used to identify a single patient by the central EHR system will be referred to herein as the master patient identifier.

Returning to method 300, once the medical data is received by the central EHR system, the master patient to whom the received medical data is related is identified. That is, the provider-specific patient identifier is matched with a master patient identifier such that the received medical data can be properly stored in a medical records database. The medical records database includes a plurality of different types of individual medical data records, and each individual data record is associated with a corresponding time and a corresponding source provider. Each individual medical data record in the medical records database relates to a single patient. In one embodiment, each medical data record is contained in its entirety in a single database table. In another embodiment, each medical data record is distributed across several database tables. The medical records database may hold records for multiple individual patients (i.e., master patients).

Figure 4:
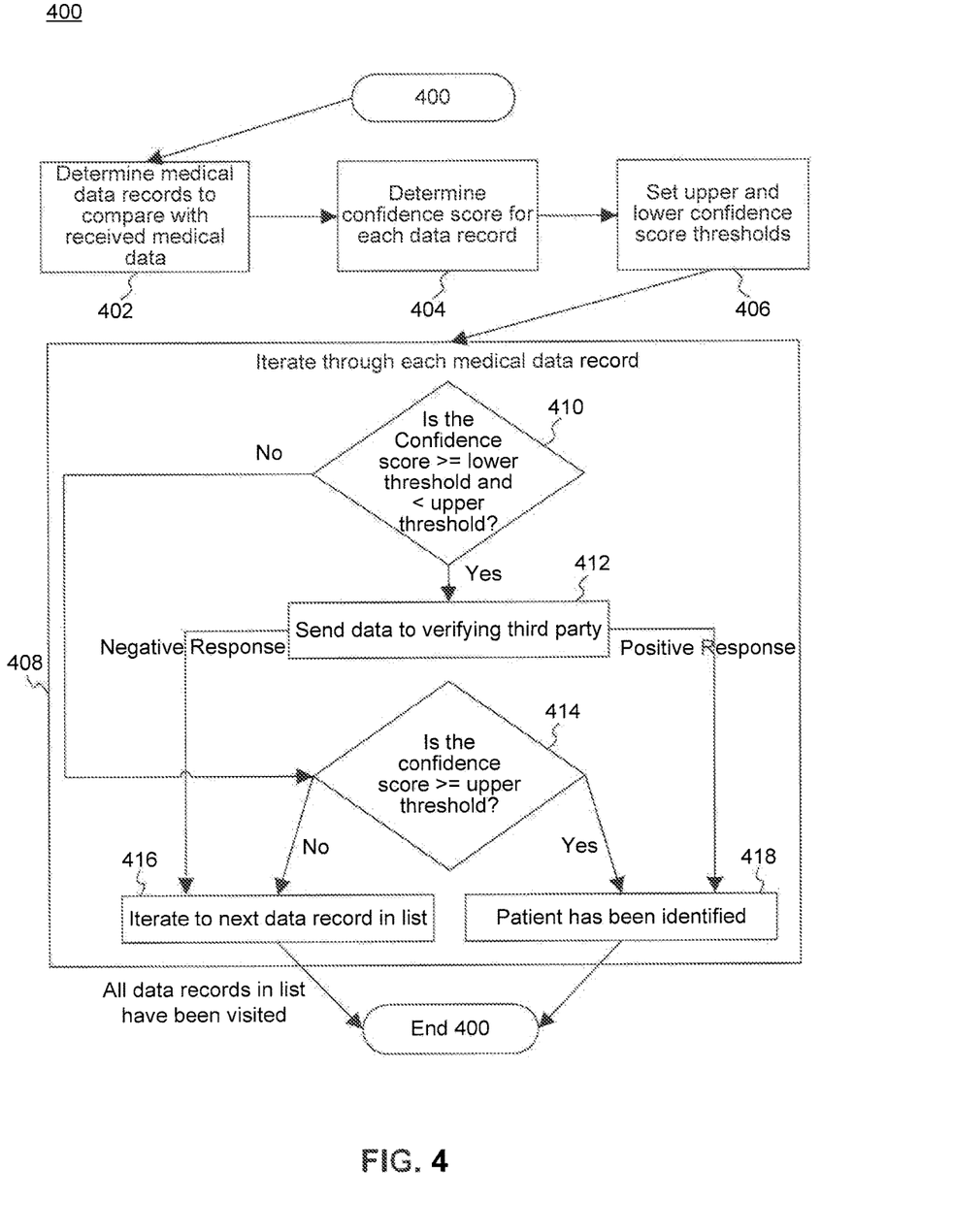
FIG. 4 is a flowchart illustrating an example method for reconciling received medical data with existing patient medical data, according to an embodiment.

To identify the master patient to whom the received medical data is related, the data may be reconciled with existing patient medical data records in the medical records database. A detailed reconciliation process is illustrated in FIG. 4. In an embodiment, once medical data from a particular source and relating to a particular patient is matched to a master patient, future medical data received from the same source and relating to the same patient may be automatically matched to the master patient without the need to repeat the reconciliation process. For example, data related to a patient's first visit to a doctor may need to undergo a reconciliation process as described above. Data related to subsequent visits to the same doctor may automatically be matched to the appropriate master patient without repeating the reconciliation process.

A provider-specific patient identifier may also be matched to a master patient identifier prior to receiving the medical data, such that future medical data received from a source provider may be matched with a master patient identifier without the need to reconcile the received medical data with existing patient data in the medical records database. For example, a patient may authorize a fitness tracking mobile device to add medical data about the patient. In an embodiment, a provider-specific patient identifier from the mobile device may be matched with the corresponding master patient identifier at the time of authorization. Then, when future medical data is received from the mobile device, the master patient to whom the medical data is related can be automatically identified based on the mobile device's provider-specific patient identifier without the need to reconcile the received medical data with existing patient medical data records.

Once the received patient data is matched with a master patient identifier, verification is performed at step 306 to confirm that the source provider associated with the received medical data is authorized to add medical data about the identified master patient to the medical records database. If the source provider is not authorized to add the received data, the method ends without writing the data to the medical records database.

If the source provider is authorized to add the received medical data, a new patient medical data record containing the received medical data is written to the database at step 308. The new patient medical data record also contains information identifying the master patient identified in step 304, and this information may be embodied in a field of the data record.

As described above with respect to FIG. 2, once all records corresponding to a master patient have been identified, that master patient's individual medical data records can be aggregated for display in a single, unified view.

FIG. 4 is a flowchart illustrating an example method for reconciling received medical data with existing patient medical data records so as to identify the specific master patient to whom the received medical data should be associated.

Method 400 begins at step 402, by identifying a list of potentially-relevant patient medical data records in the medical records database to compare with the received medical data. In one embodiment, the list may include all data records in the medical records database. In another embodiment, the list may be determined by comparing fields of the received data with fields of existing patient medical data records. For instance, the received medical data and the existing data records may each contain a social security number (SSN) field and a patient surname field. In this instance, the list may include only data records where the patient surname matches that in the received medical data, and where the SSN differs by at most one digit. This list may be dynamic, in that data records may be added to or removed from the list throughout the reconciliation process. The fields to be compared and the tolerances for differences between data present in similar fields may be set automatically by default, or by a user.

Once an initial list of potentially-relevant medical data records has been determined, a confidence score for each medical data record in the list indicating the likelihood that the received patient medical data and the medical data record relate to the same patient is determined at step 404. In an embodiment, the confidence score is at least partly determined using one or more statistical methods. An example statistical method that may be used is described in M. Jaro, "Probabilistic Linkage of Large Public Health Data Files," *Statistics in Medicine*, vol. 14, pp. 491-498 (1995), which is incorporated by reference herein in its entirety. These statistical methods use like fields between each data record and the received medical data to indicate a similarity between the data record and the received medical data. The determined confidence score may be in the form of a probability, but is not limited to such an embodiment. The list of medical data records may also be sorted. For example, the medical data records may be sorted according to each record's corresponding confidence score.

At step 406, an upper and a lower threshold are defined, and the list of data records is iterated in order. For example, if the confidence score is in the form of a probability, an upper and a lower threshold may be 0.91 and 0.82, respectively. The upper and lower thresholds are used to determine the action taken as each data record is visited. These thresholds may be determined during each reconciliation process, or they may be set in advance.

The list of data records is then processed in an iterative fashion at step 408. Iterative step 408 includes substeps 410, 412, 414, 416, and 418. At step 410, for each data record visited, it is determined whether the corresponding confidence score is greater than or equal to the lower threshold and less than the upper threshold. If such conditions are met, the received medical data and the data record, in part or in full, may be communicated to a third party for further verification at step 412. For example, the third party may be a doctor that provided the patient medical data to the system. The doctor would then verify whether the received patient medical data and the data record relate to the same patient. In another example, the third party verifier may be the patient to whom the received medical data is related.

If the response from the third party is positive, the master patient has been identified as shown in step 418 and the method terminates, returning the identified patient. If the response is negative, iteration through the list continues as shown in step 416. It should be appreciated that the verifying third party need not be a doctor or a human being, and may take another form. For example, the third party may be a trained algorithm that confirms whether the received patient medical data belongs to the master patient identified. It should also be appreciated that, in an embodiment, iteration of the list may continue while waiting for a response from the third party.

Returning to step 410, if the conditions are not met, method 400 proceeds to step 414. At step 414, it is determined whether the corresponding confidence score of the data record is greater than or equal to the upper threshold. If so, this indicates that the received patient medical data and the data record likely relate to the same patient. The method then terminates, returning the master patient identified from the data record. But if the corresponding confidence score of the data record is less than the lower threshold, the method iterates to the next medical data record in the list at step 416 and repeats all steps contained in 408. A confidence score less than the lower threshold indicates that the received medical data and the data record likely do not relate to the same master patient, and so the method continues to look for more useful data records. If all data records in the list have been visited without identifying a patient, the method terminates without returning an identified master patient.

Figure 5:
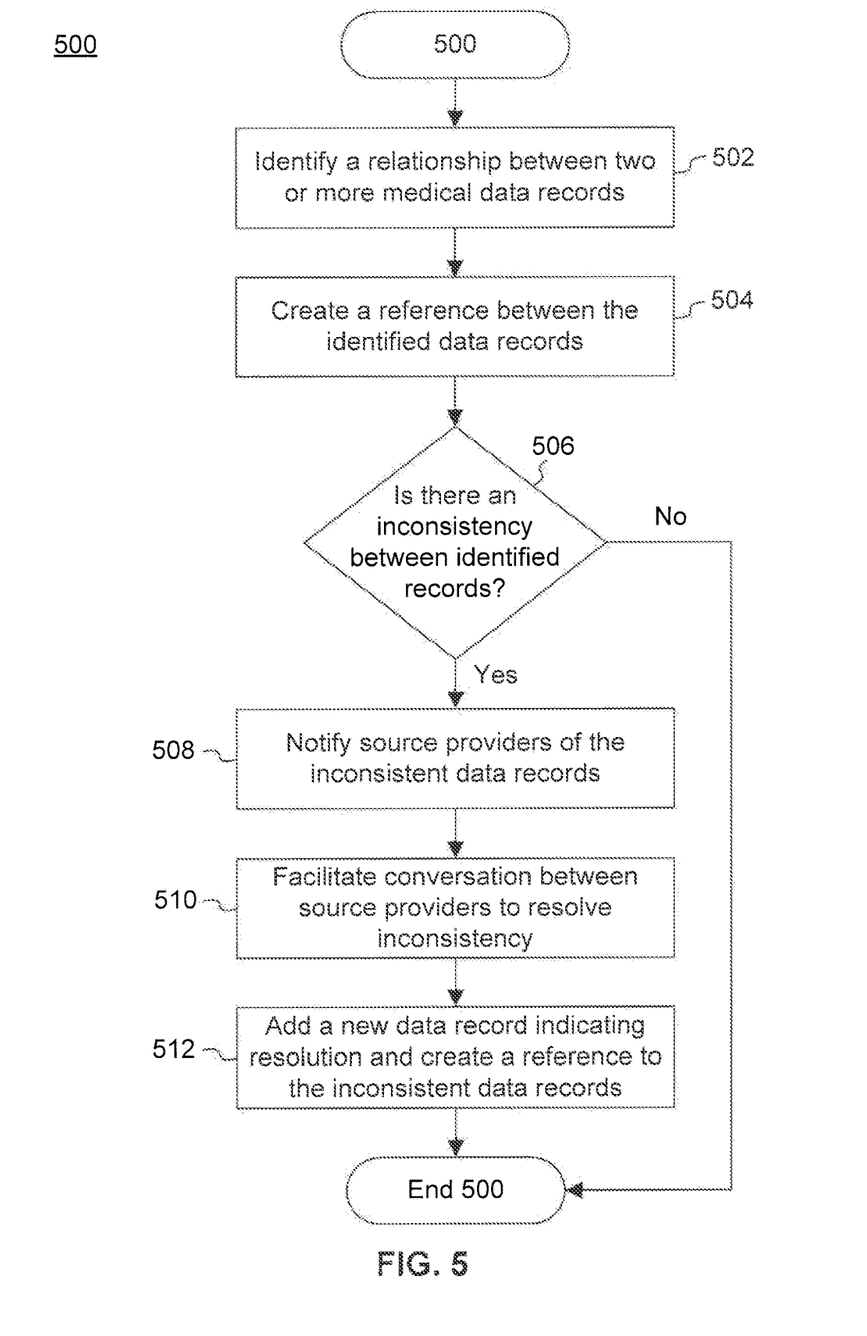
FIG. 5 is a flowchart illustrating an example method for identifying and resolving an inconsistency between two or more patient medical data records, according to an embodiment.

FIG. 5 is a flowchart illustrating an example method for identifying and resolving an inconsistency between two or more patient medical data records in the medical records database.

Method 500 begins at step 502, by identifying a relationship between two or more of the plurality of patient medical data records in the medical records database. Such identification can be accomplished through an automatic process, or manually in response to user input. A relationship simply denotes that the identified data records are connected in some manner. For example, a patient may see a first doctor who makes first diagnosis, and a data record with this information is written to the medical records database. The patient may then see a second doctor who makes a differing diagnosis, for which a data record with this information is also written to the medical records database. A relationship may be identified connecting these two events. In another example, a patient may see a doctor who orders a laboratory test, and a data record is created to represent this encounter. The laboratory results are written to the medical records database as another data record, and a relationship tray be identified between the two records. It should be appreciated that a relationship denotes any connection between data records and is not limited to these examples.

Once a relationship is identified, a reference is created between the identified data records in step 504. In an embodiment, an entry is created in a database table designating the data records involved in the relationship. In another embodiment, the data records are updated as needed to include a reference to the same master patient identifier.

Step 506 detects whether an inconsistency exists between the data records of the identified relationship. As described above, an example of an inconsistency may be differing diagnoses by two doctors. Such detection may be performed automatically by a computing device, or it may be performed by a manual process.

At step 508, the source providers are notified of the inconsistency, and communication between these source providers is facilitated at step 510 in an effort to reach a resolution. In an embodiment, this communication is accomplished by secure messaging through the system between source providers. When a resolution is reached, a new data record is written to the medical records database at step 512.

The new data record contains the resolution and references the inconsistent data records. In this way, the method allows for efficient collaboration between separate members of a medical team. If no inconsistencies are detected between the data records of the identified relationship, method 500 terminates.

System

Figure 6:
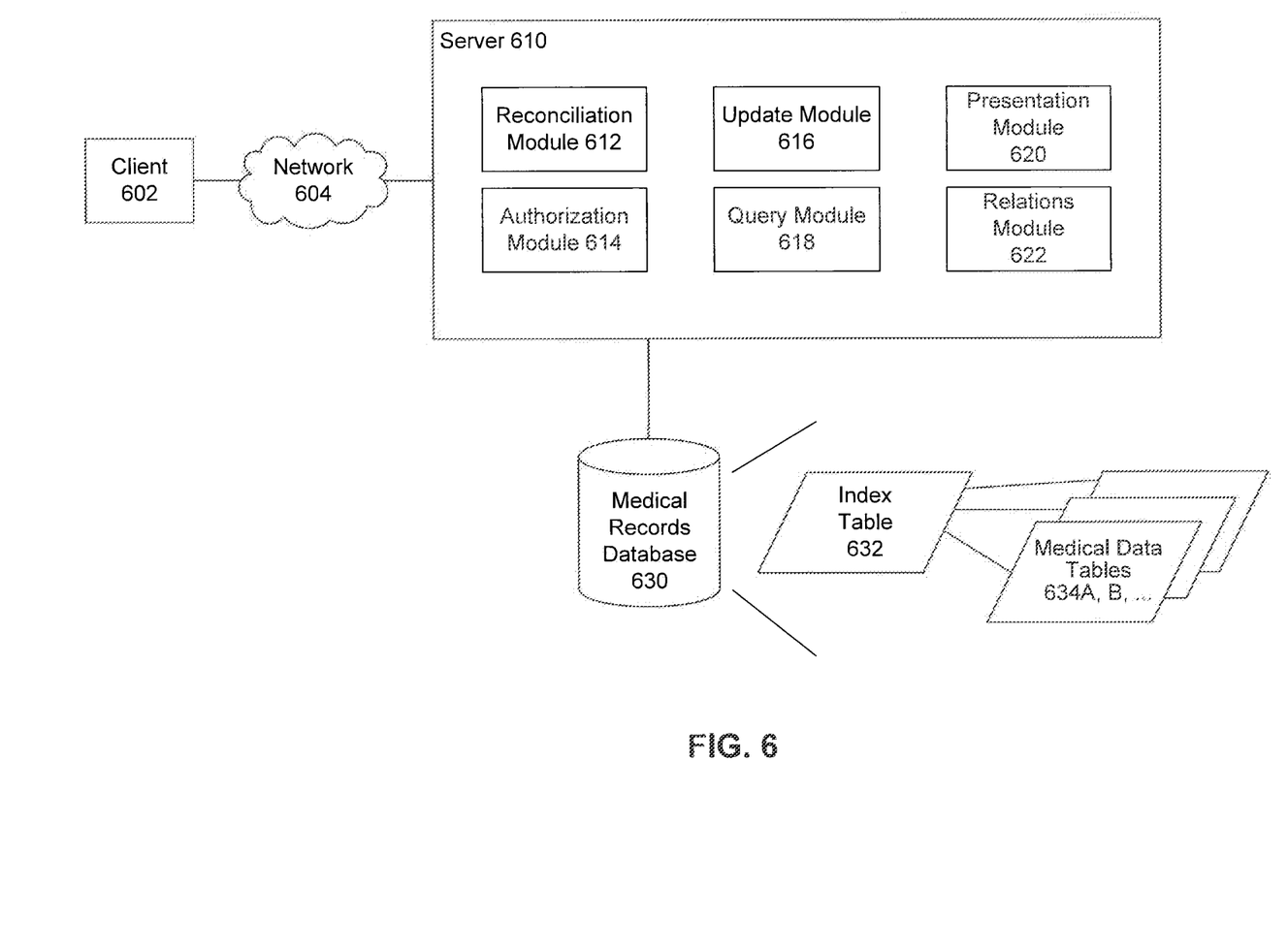
FIG. 6 is a diagram illustrating an example system for aggregating medical data from a plurality of source providers and presenting the medical data in a single, unified view, according to an embodiment.

FIG. 6 is a diagram illustrating an example system for aggregating medical data from a plurality of source providers and presenting the medical data in a single, unified view, according to an embodiment. System 600 includes a client 602 and a server 610 connected by one or more networks 604, such as the Internet. Server 610 is also coupled to a medical records database 630. Server 610 may be part of a comprehensive EHR system as described in further detail below.

Client 602 may, for example, include a web browser that enables a user to interact with an EHR system. The web browser can respond to user input by sending an HTTP request to server 610 via network 604. It another example, the user may interface with client 602 through a native application instead of a web browser, such that the native application communicates with server 610. Client 602 may be any type of computing device, such as and without limitation, a PC, laptop, or mobile device.

When receiving a request from client 602, server 610 may operate as described above with respect to FIGS. 1, 3, 4 and 5. In the embodiment of FIG. 6, server 610 includes six modules: reconciliation module 612, authorization module 614, update module 616, query module 618, presentation module 620 and relations module 622.

Reconciliation module 612 receives patient medical data via network 604 from a source provider. The source provider sends this data in the form of a request from a client 602 through network 604. Once the patient medical data is received, the data is reconciled with existing patient medical data records in the medical records database 630 in order to determine the master patient to whom the received medical data relates, as described in detail above with respect to FIG. 4.

Medical records database 630 includes a plurality of different types of patient medical data records. Each data record stored in medical records database 630 has a corresponding time and a corresponding source provider. The time may be a timestamp including both a date and time and signifying when the event described by the patient medical data record occurred. Each data record in the medical records database also relates to a single patient, and different data records in the medical records database may correspond to different patients. Medical records database 630 may be any type of structured data store, including a relational database.

As illustrated in FIG. 6, medical records database 630 may store the medical data in a plurality of different medical data tables 634A, B, . . . . Each table may store a different type of medical data. For example, medical data table 634A may store data related to patient encounters, medical data table 634B may store data related to referrals, and so on. To improve performance of database queries and updates, medical records database 630 may also include an index table 632. In an embodiment, update module 616 queries index table 632 to assist with data insertions and updates, and presentation module 620 queries index table 632 to retrieve the data needed to create a single, unified view of a patient's medical history. The index table may point to entries in medical data tables 634, which include the complete individual patient data records. Or, in an embodiment where the database is de-normalized, the index table may itself include the individual patient data records in part or in full. In this way, index table 632 may be used to improve performance of database queries and updates.

Once a patient has been identified for the received medical data, authorization module 614 verifies that the source provider associated with the medical data is authorized to add medical data about the identified patient to medical records database 630. Authorization information may be stored in medical records database 630. Authorization module 614 also performs the tasks of granting an entity permission to add and to view medical data related to a patient, as described above with respect to FIG. 1. This authorization may be limited, in that, in an embodiment, an entity may only be granted permission to view a portion of a patient's complete history of care or add only certain types of data. If the source provider is authorized to add medical data related to the identified patient, update module 616 writes a new medical data record containing the received medical data to medical records database 630.

When presenting a patient's medical data in a single, unified view, query module 618 retrieves medical data records related to the patient from medical records database 630. To identify which data records relate to the patient, query module 618 may generate one or more queries. A query may identify at least one table in medical records database 630 and may specify the appropriate data within each table to return. Execution of the query may make use of index table 632 to improve performance. Presentation module 620 organizes the returned data records into a temporally ordered list based on each data record's corresponding time. For example, the list may be ordered reverse chronologically according to each data record's corresponding time. Presentation module 620 outputs the temporally ordered list of data records for display by transmitting it, via network 604, to a client 602. For example, client 602 may include a web browser that the patient uses to view his or her complete history of care.

Relations module 622 communicates with medical records database 630 to identify relationships and inconsistencies between data records, as described above with respect to FIG. 5. A relationship may be identified by relations module 622 through its own computation, or in response to input received from client 602 via network 604. For example, a doctor may order a lab test for which a medical lab submits results. Relations module 622 may automatically identify a relationship between the data record describing the lab test order and the data record describing the lab test results. In another example, a patient may create a relationship between two data records through client 602, and relations module 622 in turn identifies this relationship. When a relationship is identified, relations module 622 creates a reference between the identified data records. In an embodiment, an entry is created in one of the medical data tables 634 designating the data records involved in the relationship.

Relations module 622 also detects inconsistencies between data records, as described above with respect to FIG. 5, either through its own computation, or in response to input received from client 602 via network 604. Relations module 622 handles the processes of notifying source providers of the inconsistent data records and facilitating conversation to resolve the inconsistency. In an embodiment, conversation is accomplished by sending secure messages from server 610 to one or more clients 602 via network 604, and server 610 receiving secure messages from one or more clients 602 via network 604. Once a resolution has been reached, update module 616 writes a new patient medical data record to medical records database 630 describing the resolution, and relations module 622 creates a reference between the new data record and the inconsistent data records.

Each of the servers and modules in FIG. 6 may be implemented on the same or different computing devices having server functionality, in hardware, software, or any combination thereof. Such computing devices can include, but are not limited to, a personal computer, a mobile device such as a mobile phone, workstation, embedded system, game console, television, set-top box, or any other computing device. Further, a computing device can include, but is not limited to, a device having a processor and memory, including a nontransitory memory, for executing and storing instructions. The memory may tangibly embody the data and program instructions. Software may include one or more applications and an operating system. Hardware can include, but is not limited to, a processor, memory, and graphical user interface display. The computing device may also have multiple processors and multiple shared or separate memory components. For example, the computing device may be a part of or the entirety of a clustered computing environment or server farm.

Figure 7:
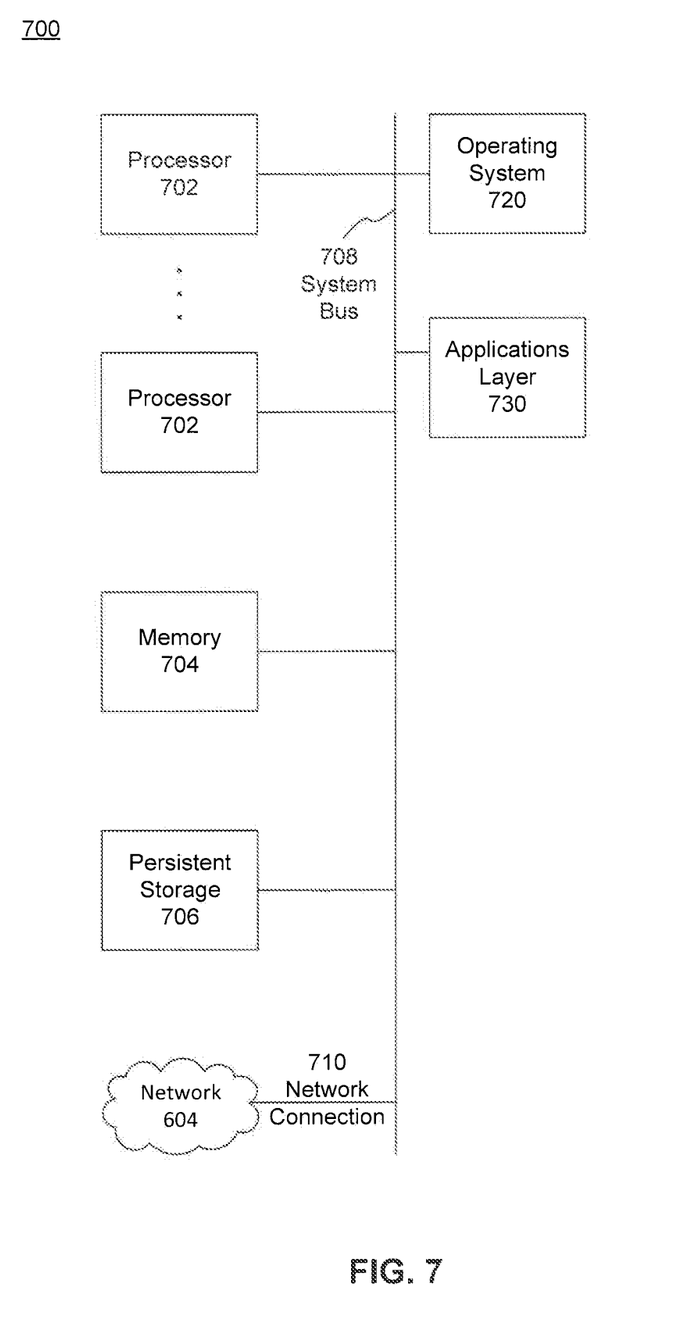
FIG. 7 is a diagram illustrating an example computing device, according to an embodiment.

FIG. 7 is a diagram illustrating an example computing device, according to an embodiment. A computing device 700 accesses a network 604 over a network connection 710 that provides computing device 700 with telecommunications capabilities. Computing device 700 uses an operating system 720 as software that manages hardware resources and coordinates the interface between hardware and software.

In an embodiment, computing device 700 contains a combination of hardware, software, and firmware constituent parts that allow it to run an applications layer 730. Computing device 700, in embodiments, may be organized around a system bus 708, but any type of infrastructure that allows the hardware infrastructure elements of computing device 700 to communicate with and interact with each other may also be used.

Processing tasks in the embodiment of FIG. 7 are carried out by one or more processors 702. However, it should be noted that various types of processing technology may be used here, including multi-core processors, multiple processors, or distributed processors. Additional specialized processing resources such as graphics, multimedia, or mathematical processing capabilities may also be used to aid in certain processing tasks. These processing resources may be hardware, software, or an appropriate combination thereof. For example, one or more of processors 702 may be a graphics-processing unit (GPU). It an embodiment, a GPU is a processor that is a specialized electronic circuit designed to rapidly process mathematically intensive applications on electronic devices. The GPU may have a highly parallel structure that is efficient for parallel processing of large blocks of data, such as mathematically intensive data common to computer graphics applications, images and videos.

In order to manipulate data in accordance with embodiments describe herein, processors 702 access a memory 704 via system bus 708. Memory 704 is nontransitory memory, such as random access memory (RAM). Memory 704 may include one or more levels of cache. Memory 704 has stored therein control logic (i.e., computer software) and/or data. For data that needs to be stored more permanently, processors 702 access persistent storage 706 via system bus 708. Persistent storage 706 may include, for example, a hard disk drive and/or a removable storage device or drive. A removable storage drive may be an optical storage device, a compact disc drive, flash memory, a floppy disk drive, a magnetic tape drive, tape backup device, and/or any other storage device/drive.

Processors 702, memory 704, and persistent storage 706 cooperate with operating system 720 to provide basic functionality for computing device 700. Operating system 720 provides support functionality for applications layer 730.

Network connection 710 enables computer device 700 to communicate and interact with any combination of remote devices, remote networks, remote entities, etc. For example, network connection 710 may allow computer device 700 to communicate with remote devices over network 604, which may be a wired and/or wireless network, and which may include any combination of LANs, WANs, the Internet, etc. Control logic and/or data may be transmitted to and from computer device 700 via network connection 710.

Applications layer 730 may house various modules and components. For example, reconciliation module 612, authorization module 614, update module 616, query module 618 and presentation module 620 may be included in applications layer 730 when computing device 700 is used as server 610.

It should be noted that computer-readable medium embodiments may include any physical medium which is capable of encoding instructions that may subsequently by used by a processor to implement methods described herein. Example physical media may include floppy discs, optical discs (e.g. CDs, mini-CDs, DVDs, HD-DVD, Blu-ray), hard drives, punch cards, tape drives, flash memory, or memory chips. However, any other type of tangible, persistent storage that can serve in the role of providing instructions to a processor may be used to store the instructions in these embodiments.

CONCLUSION

Identifiers, such as "(a)," "(b)," "(i)," "(ii)," etc., are sometimes used for different elements or steps. These identifiers are used for clarity and do not necessarily designate an order for the elements or steps.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodi-

What is claimed is:

1. A computer-implemented method for aggregating medical data from a plurality of sources, comprising:

receiving medical data associated with a corresponding source into a central EHR system, the central EHR system including a medical records database storing a plurality of different types of patient medical data records, wherein each medical data record is associated with a corresponding time and a corresponding source, wherein each medical data record includes a reference to a master patient identifier, and wherein the master patient identifier is stored in a master patient data record separate from the plurality of different types of patient medical data records;

reconciling the received medical data with existing patient medical data records in the medical records database to identify a master patient to whom the received medical data relates, wherein the reconciling further comprises:

determining a list of potentially-relevant patient medical data records in the medical records database to compare with the received medical data;

iteratively performing the following steps for each data record in the list until a master patient is identified or until all data records have been visited:

determining a confidence score for the data record indicating the likelihood that the received medical data and the data record relate to the same master patient;

communicating the received medical data and the data record to a third party for verification when the confidence score for the data record is greater than or equal to a lower threshold and less than an upper threshold;

identifying the master patient to whom the data record relates as the master patient to whom the received medical data relates when a positive response is received from the third party; and identifying the master patient to whom the data record relates as the master patient to whom the received medical data relates when the confidence score for the data record is greater than or equal to the upper threshold;

verifying that the source associated with the received medical data is authorized to add medical data related to the identified master patient;

writing a new patient medical data record to the medical records database, the new patient medical data record comprising the received medical data, a provider-specific patient identifier received from the source associated with the received medical data, and a reference to a master patient data record containing a master patient identifier corresponding to the identified master patient; and creating, in the medical records database, a link between the provider-specific patient identifier and the master patient identifier corresponding to the identified master patient, wherein when additional medical data is received from the corresponding source, the additional medical data is correlated to the master patient identifier based upon the link.

2. The method of claim 1, further comprising:

receiving additional medical data associated with the corresponding source into the central EHR system;

automatically identifying the master patient based on the link between the provider-specific patient identifier and the master patient identifier corresponding to the identified master patient; and writing an additional new patient medical data record for the identified master patient to the medical records database, the additional new patient medical data record comprising the received additional medical data.

3. The method of claim 1, further comprising:

authorizing an entity to view patient medical data related to the master patient; and authorizing an entity to add patient medical data related to the master patient to the medical records database.

4. The method of claim 3, wherein patient medical data records related to the sexual history of the master patient are made private from all entities excluding the master patient.

5. The method of claim 3, wherein patient medical data records related to the psychiatric history of the master patient are made private from all entities excluding the master patient.

6. The method of claim 3, wherein an entity is authorized to view only a portion of the plurality of patient medical data records related to a master patient.

7. The method of claim 1, further comprising: identifying a relationship between two or more of the plurality of patient medical data records in the medical records database that correspond to the identified master patient; and creating a reference between the identified data records.

8. The method of claim 7, further comprising: detecting an inconsistency between two or more of the data records of the identified relationship; notifying the corresponding sources of the inconsistent data records; facilitating communication between said sources; receiving a resolution for the detected inconsistency; and writing a new patient medical data record to the medical records database comprising the resolution, the data record referencing the inconsistent data records.

9. The method of claim 1, further comprising: retrieving the patient medical data records related to the identified master patient from the medical records database; temporally ordering the patient medical data records in a list according to the data records' corresponding time; and presenting the ordered list in a single temporal view.

10. A system for aggregating medical data from a plurality of sources, comprising:

a computing device;

a medical records database that stores a plurality of different types of patient medical data records, each medical data record associated with a corresponding time and a corresponding source, wherein each medical data record includes a reference to a master patient identifier, and wherein the master patient identifier is stored in a master patient data record separate from the plurality of different types of patient medical data records;

a reconciliation module, implemented on the computing device, configured to receive medical data associated with a corresponding source and reconcile the medical data with existing patient medical data records in the medical records database to identify a master patient to whom the medical data relates, wherein to reconcile the medical data the reconciliation module is further configured to:

determine a list of potentially-relevant patient medical data records in the medical records database to compare with the received medical data;

iteratively perform the following steps for each data record in the list until a master patient is identified or until all data records have been visited:
  determine a confidence score for the data record indicating the likelihood that the received medical data and the data record relate to the same master patient;
  communicate the received medical data and the data record to a third party for verification when the confidence score for the data record is greater than or equal to a lower threshold and less than an upper threshold;
  identify the master patient to whom the data record relates as the master patient to whom the received medical data relates when a positive response is received from the third party; and
  identify the master patient to whom the data record relates as the master patient to whom the received medical data relates when the confidence score for the data record is greater than or equal to the upper threshold;
an authorization module, implemented on the computing device, configured to verify the source associated with the received medical data is authorized to add medical data related to the master patient identified by the reconciliation module; and
an update module, implemented on the computing device, configured to:
  construct a patient medical data record for the identified master patient comprising the received medical data, a provider-specific patient identifier received from the source associated with the received medical data, and a reference to a master patient data record containing a master patient identifier corresponding to the identified master patient;
  write the constructed patient medical data record to the medical records database; and
  create, in the medical records database, a link between the provider-specific patient identifier and the master patient identifier corresponding to the identified master patient, wherein when additional medical data is received from the corresponding source, the additional medical data is correlated to the master patient identifier based upon the link.

11. The system of claim 10, wherein the authorization module is further configured to:
  authorize an entity to view patient medical data related to the master patient; and
  authorize an entity to add patient medical data related to the master patient to the medical records database.

12. The system of claim 11, wherein the authorization module is further configured to authorize an entity to view only a portion of the plurality of patient medical data records related to the master patient.

13. The system of claim 11, wherein the authorization module is further configured to make private all patient medical data records related to the sexual history of the master patient from all entities excluding the master patient.

14. The system of claim 11, wherein the authorization module is further configured to make private all patient medical data records related to the psychiatric history of the master patient from all excluding the master patient.

15. The system of claim 10, further comprising a relations module, implemented on the computing device, configured to:
  identify a relationship between two or more of the plurality of patient medical data records in the medical records database that correspond to the identified master patient; and
  create a reference between the identified data records.

16. The system of claim 15, wherein the relations module is further configured to:
  detect an inconsistency between two or more of the data records of the identified relationship;
  notify the corresponding sources of the inconsistent data records;
  facilitate communication between said sources;
  receive a resolution for the detected inconsistency; and
  write a new patient medical data record to the medical records database comprising the resolution, the data record referencing the inconsistent data records.

17. The system of claim 10, further comprising:
  a query module, implemented on the computing device, configured to retrieve the patient medical data records related to the identified master patient from the medical records database; and
  a presentation module, implemented on the computing device, configured to:
    temporally order the medical data records related to a patient in a list according to the data records' corresponding time, and
    output the ordered list to another device for display, such that the ordered list is presented in a single temporal view.

18. A program storage device tangibly embodying a program of instructions executable by at least one machine to perform a method for aggregating medical data from a plurality of sources, said method comprising:
  receiving medical data associated with a corresponding source into a central EHR system, the central EHR system including a medical records database storing a plurality of different types of patient medical data records, wherein each medical data record is associated with a corresponding time and a corresponding source, wherein each medical data record includes a reference to a master patient identifier, and wherein the master patient identifier is stored in a master patient data record separate from the plurality of different types of patient medical data records;
  reconciling the received medical data with existing patient medical data records in the medical records database to identify a master patient to whom the received medical data relates, wherein the reconciling further comprises:
    determining a list of potentially-relevant patient medical data records in the medical records database to compare with the received medical data;
    iteratively performing the following steps for each data record in the list until a master patient is identified or until all data records have been visited:
      determining a confidence score for the data record indicating the likelihood that the received medical data and the data record relate to the same master patient;
      communicating the received medical data and the data record to a third party for verification when the confidence score for the data record is greater than or equal to a lower threshold and less than an upper threshold;
      identifying the master patient to whom the data record relates as the master patient to whom the received medical data relates when a positive response is received from the third party; and identifying the master patient to whom the data record relates as the master patient to whom the received medical data relates when the confidence score for the data record is greater than or equal to the upper threshold;

verifying that the source associated with the received medical data is authorized to add medical data related to the identified master patient;

writing a new patient medical data record to the medical records database, the medical data record comprising the received medical data, a provider-specific patient identifier received from the source associated with the received medical data, and a reference to a master patient data record containing a master patient identifier corresponding to the identified master patient; and creating, in the medical records database, a link between the provider-specific patient identifier and the master patient identifier corresponding to the identified master patient, wherein when additional medical data is received from the corresponding source, the additional medical data is correlated to the master patient identifier based upon the link.

19. The program storage device of claim 18, the method further comprising:

authorizing an entity to view patient medical data related to the master patient; and authorizing an entity to add patient medical data related to the master patient to the medical records database.

* * * * *